United States Patent [19]

Parham et al.

[11] Patent Number: 5,032,670

[45] Date of Patent: Jul. 16, 1991

[54] COPOLYMERIZED ANTHRAQUINONE-POLYESTER COLOR CONCENTRATES

[75] Inventors: William W. Parham; James J. Krutak; Max A. Weaver; Clarence A. Coates, Jr.; Terry A. Oldfield, all of Kingsport, Tenn.

[73] Assignee: Eastman Kodak Company, Rochester, N.Y.

[21] Appl. No.: 400,423

[22] Filed: Aug. 30, 1989

[51] Int. Cl.$^5$ .................. C08G 2/00; C08G 12/00; C09B 1/16
[52] U.S. Cl. ............................ 528/220; 528/226; 528/228; 528/288; 528/291; 528/292; 8/643; 8/647; 552/238
[58] Field of Search ............. 552/238; 528/226, 289, 528/290, 291, 292, 288, 220, 228; 8/647, 643

[56] References Cited

U.S. PATENT DOCUMENTS

| | | |
|---|---|---|
| 3,235,322 | 2/1966 | Tahaka et al. .......... 552/238 |
| 4,144,252 | 3/1979 | Wang et al. ............ 8/647 |
| 4,267,306 | 5/1981 | Davis et al. ........... 528/226 |
| 4,314,808 | 2/1982 | Jacquet et al. ........ 8/647 |
| 4,359,570 | 11/1982 | Davis et al. ........... 528/289 |
| 4,403,092 | 9/1983 | Davis et al. ........... 528/290 |
| 4,763,371 | 8/1988 | Parton ................... 8/647 |

FOREIGN PATENT DOCUMENTS 47-13384 4/1972 Japan .
838716 6/1960 United Kingdom ............ 8/647
852646 10/1960 United Kingdom ............ 8/647

*Primary Examiner*—C. Warren Ivy
*Assistant Examiner*—Raymond Covington
*Attorney, Agent, or Firm*—Bernard J. Graves, Jr.; J. Frederick Thomsen; William P. Heath, Jr.

[57] ABSTRACT

Disclosed are color concentrate compositions which comprise a polyester having copolymerized therein at least 0.5 weight percent of an anthraquinone colorant compound having the formula

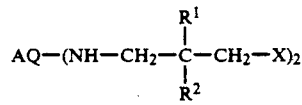

wherein AQ is a 1,5- or 1,8-anthraquinonylene radical; $R^1$ and $R^2$ are the same or different and are unsubstituted or substituted alkyl, cycloalkyl or aryl; and X is a group reactive with at least one of the functional groups of the monomers from which the polyester is prepared. Amorphous polyesters and partially-crystalline polyesters are preferred embodiments of the color concentrates. Also disclosed are colored semicrystalline powders which may be obtained from the amorphous and partially-crystalline color concentrates by a dissolution-crystallization-precipitation procedure.

28 Claims, No Drawings

COPOLYMERIZED ANTHRAQUINONE-POLYESTER COLOR CONCENTRATES

This invention pertains to polyester color concentrates comprising a polyester having copolymerized therein colored residues of at least one polyester-reactive, thermally-stable anthraquinone compound. The color concentrates may be used to impart bluish-red shades and colors to various polymeric materials, shaped articles fabricated of and coatings formulated from such polymeric materials and, especially, cosmetics and home care products where non-extractability of the colorant material is an important consideration. This invention also pertains to colored semicrystalline powders derived from the color concentrates.

Plastics, paints, printing inks, rubber, cosmetics and similar materials typically are colored by organic pigments when superior brilliance and tinctorial strength are important. Toxicity considerations have been a chronic problem relative to the use of organic pigments since some have been shown to be potential carcinogens and to cause contact dermatitis. Plastics usually contain various additives such as fillers, plasticizers, colorants, etc. The polymeric base of such plastics normally does not produce allergic or other adverse reactions by themselves but leachable or extractable additives are known [Fregert, Manual of Contact Dermatitis, Munkaard Denmark (2nd Ed. 1981)] to cause contact dermatitis.

The color concentrates provided by this invention have the colorants incorporated into the polymer chain so that the colorant will not be leachable, sublimable or extractable and will not migrate or exude from compositions colored with the color concentrates. The colored semicrystalline powders of our invention may be formulated into a wide variety of products such as cosmetics, household care products and the like which do not pose any risk or hazard to humans since exposure to toxic molecules which may be absorbed by the body is essentially eliminated. The amorphous and semi-crystalline color concentrates are preferred for coloring thermoplastic polymeric materials such as polyesters, polycarbonates, polyamides, cellulose esters, polyurethanes, polyolefins, etc. by conventional melt or solution blending techniques.

It is known to color thermoplastic polymeric materials using color concentrates consisting of physical admixtures of polymers and colorants. However, the use of such physical admixtures to color polymeric materials such as polyesters, e.g., poly(ethylene terephthalate) and blends thereof, presents a number of problems:

(1) Colorant migration during drying of the colored polymer pellets.

(2) Colorant migration during extrusion and colorant accumulation on dies which can cause film rupture and shut-downs for clean-up, etc. Such colorant migration and accumulation result in time consuming and difficult clean-up when a polymer of another color is subsequently processed in the same equipment.

(3) Colorants may not mix well, for example, when using two or more color concentrates to obtain a particular shade.

(4) Colorants may diffuse or exude during storage of the colored polymeric material.

Japanese Patent 72-13,384 discloses the coloration of polyesters for use in manufacturing colored fibers by incorporating certain anthraquinones bearing one or two reactive groups in the monomers from which the polyesters are prepared. The reactive groups are present on the alkyl moiety of alkylamino groups and have the formula -X-R-O-Y wherein X is NH or O, R is alkylene and Y is H or acetyl. These reactive anthraquinone compounds, i.e., those disclosed in Japanese Patent 72-13,384, decompose and, as a result, change color when they are added early in the synthesis of polyesters, e.g., prior to the polycondensation step. Decomposition results in a shift in the visible absorption curve and a loss of light absorption at the desired wavelength. It also is known that low concentrations, e.g., up to 5000 parts per million, of other anthraquinone compounds can be reacted with or copolymerized in polyesters to produce a colored polyester material from which the anthraquinone colorant is non-extractable. See, for example, U.S. Pat. Nos. 4,267,306, 4,359,570 and 4,403,092. Typically, an anthraquinone compound bearing one or more polyester-reactive groups, e.g., hydroxyl, carboxy or alkoxycarbonyl, is reacted into the polyester at some stage of the polyester's preparation. Thus, it is essential that the reactive anthraquinone compound be stable at the high temperatures, e.g., up to 300° C., employed during the manufacture of high molecular weight, linear polyesters.

The color concentrates provided by this invention comprise a polyester having copolymerized therein at least 0.5 weight percent, based on the weight of the polyester, or more of the residue of one or more anthraquinone compounds having the formula

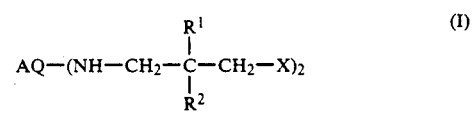

wherein

AQ is a 1,5. or 1,8-anthraquinonylene radical, i.e., radicals having the structure

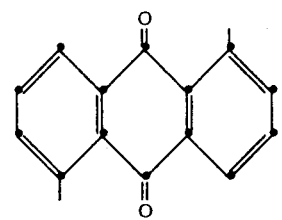

and

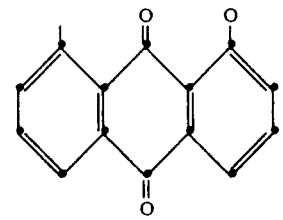

$R^1$ and $R^2$ are the same or different and are unsubstituted or substituted alkyl, cycloalkyl or aryl; and X is a group reactive with at least one of the functional groups of the monomers from which the polyester is prepared.

The anthraquinone compounds of formula (I) and the reacted residues thereof possess the advantage of being sufficiently thermally stable to permit their copolymerization with polyesters by adding them at the start or at an early stage of the polyester preparation. Neither the anthraquinone compounds nor their reacted residues sublime under polymerization conditions and the residues are not extractable from the polyesters. The thermal stability of the anthraquinone compounds is particularly important in the preparation of the color concentrates, i.e., polyesters containing from 0.5 to as high as 55 weight percent of anthraquinone colorant residue. The color concentrates are advantageous in that the colorant moiety (1) is stable to light, heat and chemicals, (2) is resistant to sublimation, heat migration, bleeding and leaching by solvents, (3) possesses high color value or chroma and visible light absorption characteristics which allows the color concentrates to be combined with yellow and/or blue (cyan) color concentrates to provide a range of colors, (4) is safe to humans and the environment.

The nitrogen atom of -NH- of the reactive group

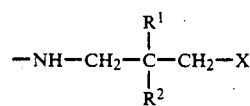

is bonded directly to a nuclear atom, i.e., a ring carbon atom, of anthraquinone nucleus AQ. The reactive anthraquinone compounds function as a copolymerizable monomer and are present within the polymer chain of the polyester, e.g.,

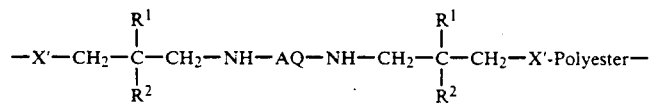

wherein AQ, $R^1$ and $R^2$ are defined above and $X'$ is the residue of reactive substituent X, e.g., -O-,

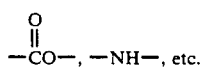

The alkyl, cycloalkyl and aryl radicals represented by $R^1$ and $R^2$ may be unsubstituted or substituted and may contain up to about 10 carbon atoms. $R^1$ and $R^2$ preferably are each lower alkyl, i.e., alkyl of up to about 4 carbon atoms, especially methyl.

Examples of the reactive groups which X may represent include hydroxy, carboxy, an ester radical, amino, alkylamino, and the like. The ester radicals may be any radical having the formula

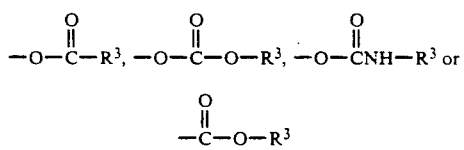

wherein $R^3$ is an unsubstituted or substituted alkyl, cycloalkyl or aryl radical, preferably unsubstituted alkyl, e.g., alkyl of up to about 8 carbon atoms, or phenyl, and most preferably, lower alkyl, e.g., methyl and ethyl. Reactive group X preferably is hydroxy or alkanoyloxy of up to about 4 carbon atoms, e.g., acetoxy. Reactive radical

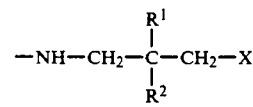

most preferably is 2,2-dimethyl-3-hydroxypropylamino.

The anthraquinone compounds described hereinabove may be prepared using known procedures and anthraquinone reactants, or procedures and/or reactants analogous thereto, wherein an anthraquinone reactant containing amine-displaceable groups is reacted with an amine:

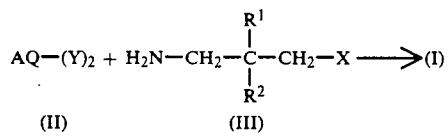

wherein Y is a displaceable substituent such as halogen, nitro and sulfo and AQ, $R^1$, $R^2$ and X are defined above. Typical synthesis procedures are described in E. Barnett, *Anthracene and Anthraquinone*, Bailliere, Tindall and Cox, London, 1921; H. A. Lubs, Editor, *The Chemistry of Synthetic Dyes and Pigments*, Reinhold Publishing Corporation, New York, 1955; and H. E. Fierz-David and L. Blangley, *Fundamental Process of Dye Chemistry*, Interscience Publishers, Inc., New York, 1949. The preferred anthraquinone reactants (II) are 1,5- and 1,8-dichloroanthraquinone. Displacement of halogen may be carried out by heating a dihaloanthraquinone with excess amine (III) at about 125 to 130° C. for several hours. Solvents such as glycol ethers, diglycol ethers, N,N-dimethylformamide, alcohols, tetrahydrothiophene-S,S-dioxide (sulfolane) and the like may be used advantageously. The use of acid acceptors such as sodium carbonate, sodium bicarbonate, sodium acetate and the like, other than excess amine (III), may be advantageous in the synthesis of some compounds. Dinitroanthraquinone reactants usually are reacted as a mixture of the 1,5- and 1,8-isomers to produce isomeric mixtures of anthraquinone compounds of formula (I).

Anthraquinone compounds of formula (I) wherein X is hydroxy may be converted to compounds in which X is a different reactive group. Thus, hydroxy group X may be converted to an ester group by the reaction of the former group with various acylating agents such as carboxylic acid chlorides, carboxylic acid anhydrides, chloroformate esters, isocyanates and the like. The hydroxy group may be converted to a halogen substituent with a halogenating agent such as a thionyl halide or phosphorus oxychloride followed by reaction with ammonia to obtain the compound wherein X is amino. The halogen-substituted compound also may be reacted with an inorganic cyanide such as an alkali cyanide to obtain an intermediate nitrile which can be hydrolyzed under acidic conditions to obtain anthraquinone compounds of formula (I) wherein X is carboxy.

Amines of formula (III) are known compounds and/or can be prepared by published procedures. Generally, the amines may be obtained by reacting an aldehyde with ammonia at elevated pressures and temperatures in the presence of a hydrogen and a hydrogenation catalyst such as Raney nickel:

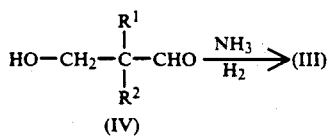

wherein $R^1$ and $R^2$ are defined above [U.S. Pat. No. 2,618,658]. Aldehydes (IV) may be synthesized by the condensation of a branched-chain aldehyde with formaldehyde in the presence of a base such as sodium or potassium carbonate according to well-known processes [E. T. Stiller et al, J. Amer. Chem. Soc., 62, 1785 (1940)]. Another means for the preparation of amines (III) involves the reaction of di-substituted propiolactones with hydrazine to give the corresponding hydrazides which are converted to amines (III) upon reduction [B.I.R. Nicolaus, J. Org. Chem., 26, 2253 (1961)].

The reactive anthraquinone compounds of formula (I) and their preparation are further illustrated by the following examples.

EXAMPLE 1

A mixture of 1,5-dichloroanthraquinone (138.0 g, 0.5 mol), 3-amino-2,2-dimethylpropanol (206.0 g, 2.0 mol) and 2-ethoxyethanol (1L) is heated at about 130° C. for 22 hours with good agitation. The dark red reaction mixture is cooled to about 40° C. and demineralized water (3L) is added to precipitate the product, 1,5-bis-[(3-hydroxy 2,2-dimethylpropyl)amino]anthraquinone, which is collected by filtration, washed with demineralized water and air dried to yield 203.0 g of product (99% of theory). Highly crystalline product (168 g, 82% of theory) is obtained by reslurrying the crude product in hot methanol, cooling the slurry to room temperature, collecting the solids by filtration, washing with methanol and drying in air. Further purification, if required, is accomplished by heating one part of the product in ten parts N,N-dimethylformamide in the presence of charcoal, filtering hot, cooling, collecting by filtration, washing with methanol and drying in air. The structure of the product is supported by mass spectrometry. The product exhibits a λmax at 528 nm (εmax=14,662) in methylene chloride.

EXAMPLE 2

A mixture of 1,8-dichloroanthraquinone (13.8 g, 0.05 mol), 3-amino-2,2-dimethylpropanol (20.6 g, 0.20 mol) and 2-ethoxyethanol (100 mL) is heated at about 130° C. for 20 hours. The reaction mixture is drowned into water (1L) and the mixture is acidified with concentrated hydrochloric acid. The product, 1,8 -bis[(3-hydroxy-2,2-dimethylpropyl)amino]anthraquinone, is obtained in an essentially quantitative yield by filtering, washing with water and drying in air. Recrystallization from toluene, followed by filtration, washing with hexane and air drying gives 16.0 g of purified crystalline product. The product may be purified further by recrystallization from methanol. Thin layer chromatography shows that the product contains only one colored component and mass spectrometry analysis is consistent with 1,8-bis[(3-hydroxy-2,2-dimethylpropyl)amino]anthraquinone. The bluish-red product has an absorption maximum at 556 nm and an extinction coefficient (ε) of 12,228 in methylene chloride.

COMPARATIVE EXAMPLE 1

A mixture of 1,5-dichloroanthraquinone (138.0 g, 0.50 mol), ethanolamine (200 g, 3.3 mol) and 2-ethoxyethanol (1.0L) is heated at reflux for 20 hours with good stirring. The dark red reaction mixture is cooled and demineralized water (1.5L) is added to precipitate the product, 1,5-bis(2-hydroxyethylamino)anthraquinone, which is collected by filtration, washed with water (500 mL) and then methanol (500 mL) and dried in air. The product is purified by recrystallizing from N,N-dimethylformamide (2L) in the presence of charcoal. The yield is 104 g (63.8% of theory) of pure product which has an absorption maximum at 520 nm (ε=13,667) in the visible absorption spectrum in N,N-dimethylformamide.

Additional anthraquinone compounds which may be utilized in the preparation of our novel color concentrates are set forth in Table I. These compounds may be prepared by the procedures referred to herein and conform to formula (I). The heading "Positions" in Table I refers to the positions of the reactive group

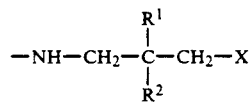

on the anthraquinone nucleus.

TABLE I

| Example | $R^1$, $R^2$ | X | Positions |
| --- | --- | --- | --- |
| 3 | di-CH₃ | —OOCCH₃ | 1,5 |
| 4 | di-CH₃ | —OOCOC₂H₅ | 1,5 |
| 5 | di-CH₃ | —OOCCH(CH₃)₂ | 1,5 |
| 6 | di-CH₃ | —OOCC₆H₅ | 1,5 |
| 7 | di-CH₃ | —OOCC₆H₁₁ | 1,5 |
| 8 | di-CH₃ | —OOCOC₆H₅ | 1,5 |
| 9 | di-CH₃ | —OOCNHC₂H₅ | 1,5 |
| 10 | di-CH₃ | —OOCNHC₆H₅ | 1,5 |
| 11 | di-CH₃ | —OOCC₆H₄-4-COOCH₃ | 1,5 |
| 12 | di-C₂H₅ | —OH | 1,5 |
| 13 | —CH₃, —CH₂CH(CH₃)₂ | —OH | 1,5 |
| 14 | di-C₆H₅ | —OH | 1,5 |
| 15 | —C₆H₅, —C₂H₅ | —OH | 1,5 |
| 16 | —C₆H₅, —CH₂C₆H₅ | —OH | 1,5 |
| 17 | —C₆H₁₁, —CH₃ | —OH | 1,5 |
| 18 | —C₆H₅, —CH₃ | —OH | 1,5 |

TABLE I-continued

| Example | R¹, R² | X | Positions |
|---|---|---|---|
| 19 | —CH₃, —C=CHCH=CHS | —OH | 1,5 |
| 20 | —C₂H₅, —C=CHCH=CHO | —OH | 1,5 |
| 21 | di-CH₃ | —COOH | 1,5 |
| 22 | —C₂H₅, —CH₃ | —COOCH₃ | 1,5 |
| 23 | di-CH₃ | —NH₂ | 1,5 |
| 24 | —CH₂C₆H₅, —CH₃ | —NHC₂H₅ | 1,5 |
| 25 | di-CH₃ | —NHCH₃ | 1,5 |
| 26 | di-CH₃ | —NHCH₂C₆H₅ | 1,5 |
| 27 | di-CH₃ | —NHCH₂C₆H₁₁ | 1,5 |
| 28 | di-CH₃ | —NHC₆H₅ | 1,5 |
| 29 | di-CH₃ | —OOCC₂H₅ | 1,8 |
| 30 | di-CH₃ | —OOCOCH₃ | 1,8 |
| 31 | di-CH₃ | —COOH | 1,8 |
| 32 | di-CH₃ | —COOCH₃ | 1,8 |
| 33 | di-CH₃ | —COOCH₂CH₂OH | 1,8 |
| 34 | di-CH₃ | —COOCH₂CH₂CN | 1,8 |
| 35 | di-CH₃ | —COOCH₂C₆H₅ | 1,8 |
| 36 | di-CH₃ | —COO(CH₂CH₂O)₂H | 1,8 |
| 37 | di-CH₃ | —NH₂ | 1,8 |
| 38 | di-CH₃ | —NHC₂H₅ | 1,8 |
| 39 | di-CH₃ | —COOC₆H₅ | 1,8 |
| 40 | —CH, —C₂H₅ | —OH | 1,8 |
| 41 | —CH₃, —C₆H₅ | —OH | 1,8 |
| 42 | —CH₃, —(CH₂)₄H | —OH | 1,8 |
| 43 | —CH₃, —C₆H₁₁ | —OH | 1,8 |
| 44 | di-CH₃ | —OOCC₆H₄-4-COOCH₃ | 1,8 |
| 45 | di-CH₃ | —OOCNHC₆H₄-4-CH₃ | 1,8 |
| 46 | di-CH₃ | —OOCNHCH₃ | 1,8 |
| 47 | di-CH₃ | —OOCNCH₂CH₂OCH₂CH₂ | 1,8 |
| 48 | —CH₃, —C=CHCH=CHS | —OOCC₆H₁₀-4-CH₃ | 1,8 |
| 49 | —CH₂C₆H₅, —CH=CHCH=CHO | —OOCCH₂C₆H₅ | 1,8 |
| 50 | di-CH₃ | —OOCCH₂CH₂COOH | 1,8 |
| 51 | di-CH₃ | —COOCC₆H₄-4-OCH₃ | 1,8 |
| 52 | di-CH₃ | —COOCH₂C=CHCH=CHO | 1,8 |

The color concentrates of the present invention comprise crystalline, semi-crystalline and amorphous polyesters having copolymerized therein at least 0.5 weight percent of the residues of at least one anthraquinone compound of formula (I). The concentration of the anthraquinone residue in the polyester is dependent on such factors as the end use for which a particular concentrate is designed, the polyester being used and the physical characteristics required of the color concentrate. Normally, the color concentrates will not contain more than 55 weight percent of anthraquinone residues with a concentration in the range of about 10 to 40 weight percent being more common. Typically, the polyester color concentrates have an inherent viscosity of at least 0.20 and are comprised of (i) a diacid component consisting of the residues of one or more dicarboxylic acids, (ii) a diol component consisting of the residues of one or more diols and (iii) a colorant component consisting of the residues of one or more anthraquinone compounds of formula (I). The concentration of colorant component (iii) and inherent viscosity are interrelated to the extent that the degree of polymerization and the inherent viscosity should be sufficiently high to ensure that substantially all of the colorant compound is reacted into the polymer and, preferably, into polymer chains which are not extractable. Thus, for example, when the concentration of colorant component (iii) is 20 weight percent or higher, the inherent viscosity of the polyester normally will be about 0.25 or higher.

The diacid residues may be derived from aliphatic, alicyclic, or aromatic dicarboxylic acids such as terephthalic acid, isophthalic acid, 1,4-cyclohexane. dicarboxylic acid, 1,3-cyclohexanedicarboxylic acid, succinic acid, glutaric acid, adipic acid, sebacic acid, 1,12-dodecanedioic acid, 2,6-naphthalenedicarboxylic acid and the like. In the polymer preparation, it is often preferable to derive the diacid residues from an ester-forming derivative of the dicarboxylic acid such as the dimethyl, diethyl, or dipropyl esters. The anhydrides or acid halides of these acids also may be employed where practical.

The diol components of the described polyesters may be selected from ethylene glycol, 1,2-propanediol, 1,3- propanediol, 1,4-butanediol, 2,2-dimethyl-1,3-propanediol, 1,6-hexanediol, 1,10-decanediol, 1,12-dodecanediol, 1,2-cyclohexanediol, 1,4-cyclohexanediol, 1,2-cyclohexanedimethanol, 1,3-cyclohexanedimethanol, 1,4-cyclohexanedimethanol, X,8-bis(hydroxymethyl)-tricyclo-[5.2.1.0]-decane wherein X represents 3, 4, or 5; and diols containing one or more oxygen atoms in the chain, e.g., diethylene glycol, triethylene glycol, dipropylene glycol, tripropylene glycol, 1,3- and 1,4-bis(2-hydroxyethyl)benzene and the like. In general, these diols contain 2 to 18, preferably 2 to 12 carbon atoms. Cycloaliphatic diols can be employed in their cis or trans configuration or as mixtures of both forms.

The amorphous color concentrates of our invention exhibit a glass transition temperature (Tg) and no, or only a trace of, crystallization or melting point by differential scanning calorimetry (DSC). Examples of such amorphous polyesters include those obtained by the polymerization of an anthraquinone compound of formula (I), terephthalic and/or 2,6-naphthalenedicarboxylic acid and a branched-chain diol having the formula

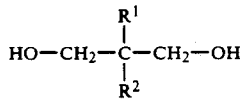

wherein $R^1$ and $R^2$ are defined hereinabove. Preferred amorphous polyester color concentrates have an inherent viscosity of about 0.2 to 0.8 and are comprised of:

(i) diacid residues comprised of at least 50, preferably at least 80, mole percent terephthalic and/or 2,6-naphthalenedicarboxylic acid residues;

(ii) diol residues comprised of at least 50, preferably at least 80, mole percent of residues of a diol having the formula

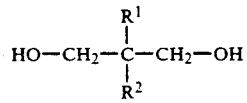

wherein $R^1$ and $R^2$ are the same or different and are lower alkyl; and (iii) residues of anthraquinone compound (I). The particularly preferred amorphous polyester color concentrates are comprised of (i) diacid residues consisting essentially of terephthalic and/or 2,6-naphthalenedicarboxylic acid residues; diol residues consisting essentially of 2,2-dimethyl-1,3-propanediol residues; and (iii) residues of anthraquinone compound (I), especially an anthraquinone compound having the formula

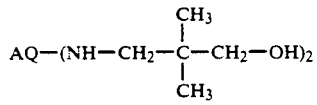

wherein AQ is a 1,5- or 1,8-anthraquinonylene radical.

Other amorphous polyesters, as defined above, suitable for preparing the colored semicrystalline powders may be obtained by employing (1) two dicarboxylic acids and one or more diols or (2) two diols and one or more dicarboxylic acids according to known procedures for obtaining amorphous polyesters. The polyester comprising a diacid component consisting of 75 mole percent terephthalic acid residues and 25 mole percent 1,4-cyclohexanedicarboxylic acid residues, a diol component consisting of 1,4-butanediol residues and residues of anthraquinone compound (I) is an example of such a polyester.

The partially-crystalline color concentrates of this invention usually exhibit a glass transition temperature, a crystallization temperature and a melting temperature by DSC. These partially-crystalline, polyester concentrates are comprised of (i) diacid residues consisting of at least 80 mole percent terephthalic acid residues, 2,6-naphthalenedicarboxylic acid residues, 1,3-cyclohexanedicarboxylic acid residues, 1,4-cyclohexanedicarboxylic acid residues or a mixture thereof, (ii) diol residues consisting of at least 50 mole percent of residues having the formula $-O-(CH_2)_m-O-$ wherein m is 4 to 12 and (iii) residues of colorant compound (I). A preferred partially-crystalline color concentrate has a melting temperature of at least 110° C. and is comprised of (i) diacid residues comprised of at least 80 mole percent terephthalic acid residues, (ii) diol residues comprised of at least 80 mole percent of residues of 1,4-butanediol and (iii) residues of colorant compound (I). An especially preferred partially-crystalline color concentrate has a melting temperature of at least 110° C. and consists essentially of (i) terephthalic acid residues, (ii) 1,4-butanediol residues and (iii) residues of 1,5-bis[(3-hydroxy-2 2,2-dimethylpropyl)amino]anthraquinone.

The colored semicrystalline powders provided by our invention may be obtained by means of a dissolution-crystallization-precipitation procedure wherein the amorphous or partially-crystalline polyester color concentrates described above are dissolved in an organic solvent from which the polymeric color concentrate is recovered in a finely divided form consisting of particles of relatively uniform size, e.g., from about 10 to 30 microns. If desired, the particle size of the colored semicrystalline powders may be reduced further by conventional grinding processes. Examples of solvents in which the amorphous and/or partially-crystalline concentrates may be dissolved include halogenated hydrocarbons such as aliphatic chlorides, e.g., methylene chloride, esters such as alkyl esters of carboxylic acids, e.g., ethyl acetate and methyl benzoate, hydrocarbons such as toluene and ethers such as tetrahydrofuran. We have found methylene chloride to be a particularly effective solvent.

The particular dissolution-crystallization-precipitation procedure utilized is not critical. The amorphous or partially-crystalline concentrate may be dissolved in a suitable solvent at elevated temperatures and then crystallized in a finely-divided state by cooling, with or without a reduction in the volume of solvent, i.e., either with or without a solution concentration step. Another useful technique involves dissolving the amorphous concentrate in an organic solvent, either at ambient or elevated temperature, and then adding to the solution another miscible solvent which causes crystallization of the colored semicrystalline powder. The use of methylene chloride as the primary solvent and an alkyl acetate such as ethyl acetate as the "crystallization-inducing" solvent has been found to be particularly efficacious. Depending on their intended utility, the colored semicrystalline powders may be extracted with a suitable organic solvent to remove relatively low molecular weight polyester oligomers. Examples of oligomerextracting solvents include ketones such as acetone, 2-pentanone, 3-methyl-2-butanone, 4-methyl-2-pentanone, 2-hexanone and 5-methyl-2-hexanone; hydrocarbons such as hexane, heptane and toluene; and ethers such as tetrahydrofuran. Another, but not preferred, dissolution-precipitation procedure involves dissolving the amorphous color concentrates in certain solvents, e.g., ethyl acetate, from which the polymeric color concentrate, after undergoing a change in morphology, precipitates.

The dissolution-crystallization-precipitation procedure alters the morphology of the amorphous and partially-crystalline polyester color concentrates in a number of respects. X-Ray diffraction analysis of the colored semicrystalline powders shows a marked increase in the crystallinity of the polyester and, while the amorphous polyester concentrates do not exhibit a melting temperature, the microcrystalline concentrates usually (almost always) exhibit a melting temperature by DSC. Although the weight average molecular weight (Mw) may increase, decrease or not be changed by the dissolution-crystallization-precipitation procedure, the number average molecular weight (Mn) always increases, the magnitude of the increase depending on the degree to which oligomeric material has been removed from the colored semicrystalline polyester powder. The polydispersity ratio (Mw:Mn) of the colored semicrystalline polyester is always less than that of the polyester concentrate from which it is prepared due to the increase in Mn (even when Mw increases, Mn increases more). Finally, the inherent viscosity of the colored semicrystalline powders normally is slightly higher than that of the color concentrate.

Processes for preparing finely divided forms of polyesters also are disclosed in U.S. Pat. Nos. 4,378,228, 4,254,207, 3,586,654, 3,931,082, 4,267,310, 4,305,864, 4,451,606, 3,674,736 and 3,669,922. The amorphous and partially-crystalline polyester color concentrates may be used in coloring various thermoplastic polymeric materials when non-extractability or non-volatility of the colorant is critical because of toxicity considerations, e.g., in rigid and flexible packaging materials for food. The concentrates and powders may be used in formulating inks, coatings, toners for impactless printing, and similar products.

Our novel color concentrates and their preparation are further illustrated by the following examples. The inherent viscosities specified herein are determined at 25° C. using 0.5 g of polymer (polyester color concentrate) per 100 mL of a solvent consisting of 60 weight percent phenol and 40 weight percent tetrachloroethane. The weight average molecular weight (Mw) and number average molecular weight values referred to herein are determined by gel permeation chromatography. The melting temperatures are determined by differential scanning calorimetry on the first and/or second heating cycle at a scanning rate of 20° C. per minute and are reported as the peaks of the transitions.

EXAMPLE 53

The following materials are placed in a 500-mL three-necked, round-bottom flask:

133.6 g (0.689 mol) dimethyl terephthalate
85.5 g (1.380 mol) ethylene glycol
0.0178 g Ti from a n-butanol solution of titanium tetraisopropoxide
54.0 g (0.132 mol) 1,5-bis[(3-hydroxy-2,2-dimethylpropyl)amino]anthraquinone The flask is equipped with a nitrogen inlet, stirrer, vacuum outlet, and condensing flask. The flask and contents are heated in a Belmont metal bath with a nitrogen sweep over the reaction mixture as the temperature is increased to 200° C. and then to 220° C. over 75 minutes. Over the next 30 minutes the temperature is increased to about 240° C. and then to about 260° C. over the next 30 minutes. The temperature is quickly raised (over about 10 minutes) to 275° C. and a vacuum is applied until the pressure is reduced to 0.5 mm Hg. The polycondensation is completed by heating the flask and contents at about 275° C. for about 45 to 60 minutes under a pressure of 0.1 to 0.5 mm Hg. The flask is removed from the metal bath and is allowed to cool while the polymer solidifies. The resulting dark red polyester, containing 30.3 weight percent of the anthraquinone colorant residue, has an inherent viscosity of 0.49.

EXAMPLE 54

The following materials are placed in a 500-mL three-necked, round-bottom flask:

135.8 g (0.70 mol) dimethyl terephthalate
94.6 g (0.91 mol) 2,2-dimethyl-1,3-propanediol
0.0177 g Ti from a n-butanol solution of titanium tetraisopropoxide
18.0 g (0.044 mol) 1,5-bis[(3-hydroxy-2,2-dimethylpropyl)amino]anthraquinone The flask is equipped with a nitrogen inlet, stirrer, vacuum outlet, and condensing flask. The flask and contents are heated in a Belmont metal bath with a nitrogen sweep over the reaction mixture as the temperature is increased to 200° C. and then to 220° C. over 90 minutes. Over the next 30 minutes the temperature is increased to about 240° C. and then to about 260° C. over the next 30 minutes. The temperature is quickly raised (over about 10 minutes) to 275° C. and a vacuum is applied until the pressure is reduced to 0.5 mm Hg. The polycondensation is completed by heating the flask and contents at about 275° C. for 75 minutes under a pressure of 0.1 to 0.5 mm Hg. The flask is removed from the metal bath and is allowed to cool while the polymer solidifies. The resulting dark red polyester, containing 30.3 weight percent of the anthraquinone colorant residue, has an inherent viscosity of 0.56, no melting temperature, a weight average molecular weight of 39,000, a number average molecular weight of 20,000 and a polydispersity value of 1.94.

EXAMPLE 55

A portion (25.0 g) of the amorphous polyester color concentrate prepared in Example 54 is granulated using a Wiley mill and dissolved in methylene chloride (200 mL) at about 25° C. with stirring. Ethyl acetate (200 mL) is added and the methylene chloride is removed by distillation. The mixture is stirred for about 12 to 15 hours (usually overnight) at about 25° C. during which time the colored semicrystalline powder separates. Acetone (200 mL) is added with stirring and the solid is collected by filtration and slurried in acetone (200 mL) and filtered four times to remove oligomers from the product which after drying weighs 23.6 g. The colored semicrystalline powder thus prepared has an inherent viscosity of 0.58, a melting temperature of 144° C., a weight average molecular weight of 38,000, a number average molecular weight of 25,000 and a polydispersity value of 1.52. The accountability of the anthraquinone colorant compound is 93% as determined by visual spectroscopy and a comparison of the absorbance of a methylene chloride solution of 1,5-bis[(3-hydroxy-2,2-dimethylpropyl)-amino]anthraquinone with the absorbance of a methylene chloride solution of the microcrystalline color concentrate. The comparison shows no shift in absorbance indicating that the colorant is not decomposed during the synthesis of the polyester.

EXAMPLE 56

The procedure of Example 54 is repeated using:
108.6 g (0.560 mol) dimethyl terephthalate
75.7 g (0.728 mol) 2,2-dimethyl-1,3-propanediol
0.0170 g Ti from a n-butanol solution of titanium tetraisopropoxide
52.0 g (0.44 mol) 1,5-bis[(3-hydroxy-2,2-dimethylpropyl)amino]anthraquinone
The dark red polyester color concentrate contains 30.6 weight percent of the residue of 1,5-bis[(3-hydroxy-2,2-dimethylpropyl)amino]anthraquinone and has an inherent viscosity of 0.47, a weight average molecular weight of 31,000, a number average molecular weight of 17,000 and a polydispersity value of 1.84.

EXAMPLE 57

The procedure described in Example 55 is repeated precisely using 25.0 g of the color concentrate prepared in Example 56 to give 22.4 g of dark red, semi-crystalline powder having an inherent viscosity of 0.49, a weight average molecular weight of 35,000, a number average molecular weight of 25,000 and a polydispersity value of 1.42. The accountability of the anthraquinone colorant by visual spectroscopy is 91.1%.

EXAMPLE 58

A portion (57.2 g) of the color concentrate prepared in Example 56 is granulated and partially dissolved in boiling ethyl acetate (480 mL) by stirring. The mixture is cooled with stirring to 25° C. at a rate of less than 1° C. per minute. Stirring is stopped and the color concentrate is allowed to precipitate and undergo solvent-induced crystallization for about 15 hours. The dark red crystalline solid is separated by filtration and slurried in acetone (300 mL) three or four times to remove any low molecular weight oligomers from the product. After the last filtration, the solid is dried to give 45.1 g of colored semicrystalline powder having a melting temperature of 122° C., a weight average molecular weight of 36,122, a number average molecular weight of 26,224 and a polydispersity value of 1.38. Color accountability, determined as described in Example 55, is 93%.

EXAMPLE 59

The procedure of Example 54 is repeated using:
84.1 g (0.43 mol) dimethyl terephthalate
58.6 g (0.56 mol) 2,2-dimethyl-1,3-propanediol
0.0165 g Ti from a n-butanol solution of titanium tetraisopropoxide
85.1 g (0.21 mol) 1,5-bis[(3-hydroxy-2,2-dimethylpropyl)amino]anthraquinone
The extremely dark red polyester color concentrate contains 51.6 weight percent of the residue of 1,5-bis-[(3-hydroxy-2,2-dimethylpropyl)amino]anthraquinone and has an inherent viscosity of 0.36.

EXAMPLE 60

The procedure described in Example 55 is repeated precisely using 25.0 g of the color concentrate prepared in Example 58 to give 22.9 g of very dark red, semi-crystalline powder.

EXAMPLE 61

A portion (75.0 g) of the color concentrate prepared in Example 58 is ground and crystallized from ethyl acetate (500 mL) as described in Example 57 to obtain 58.8 g of very dark red crystalline color concentrate with an anthraquinone colorant accountability of 93%.

EXAMPLE 62

The procedure of Example 54 is repeated using:
135.8 g (0.70 mol) dimethyl terephthalate
94.6 g (0.91 mol) 2,2-dimethyl-1,3-propanediol
0.0164 g Ti from a n-butanol solution of titanium tetraisopropoxide
0.82 g (0.21 mol) 1,5-bis[(3-hydroxy-2,2-dimethylpropyl)amino]anthraquinone
The bright red polyester color concentrate contains 0.50 weight percent of the residue of 1,5-bis[(3-hydroxy-2,2-dimethylpropyl)amino]anthraquinone and has an inherent viscosity of 0.65.

EXAMPLE 63

The procedure of Example 54 is repeated using:
113.0 g (0.70 mol) dimethyl 2,6-naphthalenedicarboxylate
62.5 g (0.91 mol) 2,2-dimethyl-1,3-propanediol
0.0170 g Ti from a n-butanol solution of titanium tetraisopropoxide
51.7 g (0.127 mol) 1,5-bis[(3-hydroxy-2,2-dimethylpropyl)amino]anthraquinone
The dark red polyester color concentrate contains 30.4 weight percent of the residue of 1,5-bis[(3-hydroxy-2,2-dimethylpropyl)amino]anthraquinone and has an inherent viscosity of 0.37.

EXAMPLE 64

The procedure of Example 54 is repeated using:
135.8 g (0.70 mol) dimethyl terephthalate
94.6 g (0.91 mol) 2,2-dimethyl-1,3-propanediol
0.0164 g Ti from a n-butanol solution of titanium tetraisopropoxide
0.82 g (0.21 mol) 1,8-bis[(3-hydroxy-2,2-dimethylpropyl)amino]anthraquinone
The dark red polyester color concentrate contains 0.50 weight percent of the residue of 1,8-bis[(3-hydroxy-2,2-dimethylpropyl)amino]anthraquinone and has an inherent viscosity of 0.67.

COMPARATIVE EXAMPLE 2

The procedure of Example 54 is repeated using:
108 6 g (0.70 mol) dimethyl terephthalate
75.7 g (0.91 mol) 2,2-dimethyl-1,3-propanediol
0.0166 g Ti from a solution of titanium tetraisopropoxide
52.0 g (0.21 mol) 1,5-bis[(2-hydroxyethyl)amino]anthraquinone
During the polycondensation, a color change from red to orange was observed, indicating decomposition of the anthraquinone compound. The polymer produced is extremely brittle and has a low inherent viscosity (0.21), further indicating decomposition of the anthraquinone colorant. Visible spectroscopy shows the polymer to contain a considerable amount of yellow-orange decomposition product in addition to the red residue of 1,5-bis[(2-hydroxyethyl)amino]anthraquinone as the absorption curve is shifted considerably from absorption maximum ($\lambda$max) at 521 nm for 1,5-bis[(2-hydroxyethyl)amino]anthraquinone (in methylene chloride) to λmax 509 for the copolymerized color concentrate.

EXAMPLE 65

The following materials are placed in a 500-mL three-necked, round-bottom flask:

145.50 g (0.750 mol) dimethyl terephthalate
101.25 g (1.125 mol) 1,4-butanediol
0.0214 g Ti from a n-butanol solution of titanium tetraisopropoxide
63.00 g (0.044 mol) 1,5-bis[(3-hydroxy-2,2-dimethylpropyl)amino]anthraquinone The flask is equipped with a nitrogen inlet, stirrer, vacuum outlet, and condensing flask. The flask and contents are heated in a Belmont metal bath with a nitrogen sweep over the reaction mixture as the temperature is increased to 200° C. The mixture is heated at 200° C. for 1.75 hours and then the temperature is raised to and maintained at 225° C. over a period of 2.25 hours. The nitrogen sweep is then stopped and vacuum is applied to lower the pressure to about 0.5 to 1.0 mm Hg. The polycondensation is completed by heating the flask and contents at about 225° C. for 1 hour under a pressure of 0.5 to 1.0 mm Hg. The vacuum is then relieved with nitrogen and methyl benzoate (125 mL) is added slowly and stirred to solution over about 10 minutes with the flask still in the metal bath. The resulting solution is transferred to a 2L beaker and stirred until crystallization occurs. Hexane (700 mL) is added slowly with stirring to dilute the slurry and keep it stirable. (Acetone, which removes more oligomeric material, also may be used.) The diluted slurry is stirred for 30 minutes, filtered and the cake is washed with hexane. The cake is twice reslurried in hexane and then dried in a vacuum oven. The resulting dark red semicrystalline polyester powder, containing 29.42 weight percent of the anthraquinone colorant residue, has an inherent viscosity of 0.202, a melting temperature of 175° C., a glass transition temperature of 66° C., a weight average molecular weight of 12,646, a number average molecular weight of 8359 and a polydispersity value of 1.51. Reslurrying the powder twice in acetone increases the non-extractability of color and raises the inherent viscosity to 0.26.

EXAMPLE 66

The procedure described in Example 65 is repeated except that the reaction mixture is heated at 200° C. for 1.75 hours and then the temperature is raised to 220° C. over 1.25 hours, then to 240° C. over 1.25 hours and finally to 270° C. over 1.25 hours. Vacuum is applied to lower the pressure to about 0.5 to 1.0 mm Hg and polycondensation is completed by heating the flask and contents at about 270° C. for 22 minutes under a pressure of 0.5 to 1.0 mm Hg. The vacuum is then relieved with nitrogen and methyl benzoate (125 mL) is added slowly and stirred to solution over about 50 minutes with the flask still in the metal bath. The resulting solution is transferred to a 2L beaker and stirred until crystallization occurs. Acetone (1L) is added slowly with stirring to dilute the slurry and keep it stirable. The diluted slurry is stirred for 30 minutes and the cake is slurried in hexane (1L). The cake is again slurried in acetone and hexane and then dried in air to yield 212.89 g (99.40% of theory) colored powder. The dark red polyester powder, containing 29.42 weight percent of the anthraquinone colorant residue, has an inherent viscosity of 0.190, a melting temperature of 172° C., a glass transition temperature of 54° C., a weight average molecular weight of 12,806, a number average molecular weight of 8903 and a polydispersity value of 1.44.

EXAMPLE 67

The following materials are placed in a 500-mL three-necked, round-bottom flask:

91.0 g (0.469 mol) dimethyl terephthalate
63.3 g (0.704 mol) 1,4-butanediol
0.01343 g Ti from a n-butanol solution of titanium tetraisopropoxide
40.0 g (0.0976 mol) 1,5-bis[(3-hydroxy-2,2-dimethylpropyl)amino]anthraquinone The flask is equipped with a nitrogen inlet, stirrer, vacuum outlet, and condensing flask. The flask and contents are heated in a Belmont metal bath with a nitrogen sweep over the reaction mixture as the temperature is increased to 200° C. and then to 220° C. over 2 hours. Over the next 30 minutes the temperature is increased to about 240° C. and then to about 260° C. over the next 30 minutes. The temperature is quickly raised (over about 10 minutes) to 275° C. and a vacuum is applied until the pressure is reduced to 0.5 mm Hg. The polycondensation is completed by heating the flask and contents at about 275° C. for 45 minutes under a pressure of 0.1 to 0.5 mm Hg. The vacuum is then relieved with nitrogen and methyl benzoate (125 mL) is added slowly and stirred to solution over about 10 minutes with the flask still in the metal bath. The resulting solution is transferred to a 2L beaker and stirred until crystallization occurs. Acetone (500 mL) is added slowly with stirring to dilute the slurry and keep it stirable. The diluted slurry is stirred for 30 minutes, filtered and the cake is washed with acetone. The cake is twice reslurried in acetone and then dried in air. The resulting dark red semicrystalline polyester powder, containing 29.77 weight percent of the anthraquinone colorant residue, has an inherent viscosity of 0.485, a melting temperature of 182° C., a weight average molecular weight of 36,927, a number average molecular weight of 23,685 and a polydispersity value of 1.59.

The invention has been described in detail with particular reference to preferred embodiments thereof, but it will be understood that variations and modifications can be effected within the spirit and scope of the invention.

We claim:

1. A color concentrate comprising a polyester having copolymerized therein at least 0.5 weight percent, based on the weight of the concentrate, of the residue of one or more anthraquinone compounds having the formula

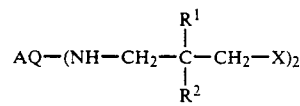

wherein
AQ is a 1,5- or 1,8-anthraquinonylene radical;
$R^1$ and $R^2$ are the same or different and are unsubstituted or substituted alkyl, cycloalkyl or aryl; and
X is a group reactive with at least one of the functional groups of the monomers from which the polyester is prepared.

2. A color concentrate according to claim 1 comprising a polyester having an inherent viscosity of at least 0.20 having copolymerized therein at least 0.5 weight percent, based on the weight of the concentrate, of the residue of one or more anthraquinone compounds having the formula

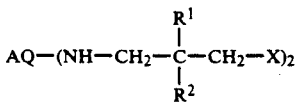

wherein
AQ is a 1,5- or 1,8-anthraquinonylene radical;
R¹ and R² are the same or different and are lower alkyl; and
X is hydroxy, carboxy, amino, alkyl amino or an ester group having the formula

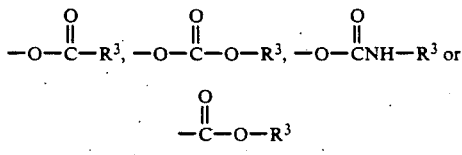

wherein R³ is an unsubstituted or substituted alkyl, cycloalkyl or aryl radical.

3. A color concentrate according to claim 1 comprising a polyester having an inherent viscosity of at least 0.20 having copolymerized therein about 10 to 40 weight percent, based on the weight of the polyester, of the residue of one or more anthraquinone compounds having the formula

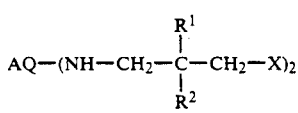

wherein
AQ is a 1,50 or 1,8-anthraquinonylene radical;
R¹ and R² are the same or different and are lower alkyl; and
X is hydroxy, carboxy, amino, alkyl amino or an ester group having the formula

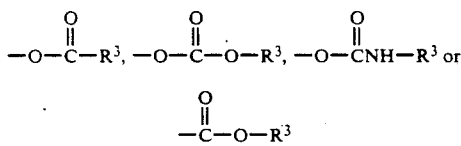

wherein R³ is alkyl or phenyl.

4. A color concentrate according to claim 1 comprising a polyester having an inherent viscosity of at least 0.20 having copolymerized therein about 10 to 40 weight percent, based on the weight of the polyester, of the residue of an anthraquinone compound having the formula

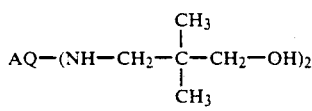

wherein AQ is a 1,5- or 1,8-anthraquinonylene radical.

5. An amorphous color concentrate comprising an amorphous polyester having copolymerized therein at least 0.5 weight percent, based on the weight of the concentrate, of the residue of one or more anthraquinone compounds having the formula

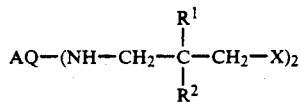

wherein
AQ is a 1,5- or 1,8-anthraquinonylene radical;
R¹ and R² are the same or different and are unsubstituted or substituted alkyl, cycloalkyl or aryl;
X is a group reactive with at least one of the functional groups of the monomers from which the polyester is prepared.

6. An amorphous color concentrate according to claim 5 comprising a polyester having an inherent viscosity of at least 0.20 comprised of:
(i) diacid residues comprised of at least 50 mole percent terephthalic and/or 2,6-naphthalenedicarboxylic acid residues;
(ii) diol residues comprised of at least 50 mole percent of the residue of a diol having the formula

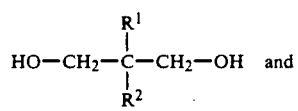

(iii) residues of one or more anthraquinone compounds having the formula

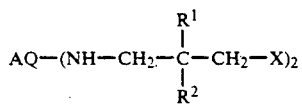

wherein
AQ is a 1,5- or 1,8-anthraquinonylene radical;
R¹ and R² are the same or different and are lower alkyl; and
X is hydroxy, carboxy, amino, alkyl amino or an ester group having the formula

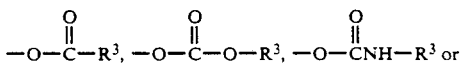

wherein R³ is an unsubstituted or substituted alkyl, cycloalkyl or aryl radical, provided that component (iii) constitutes at least 0.5 weight percent of concentrate.

7. An amorphous color concentrate according to claim 5 comprising a polyester having an inherent viscosity of 0.20 to 0.80 and a melting temperature of at least 110° C. comprised of:
(i) diacid residues comprised of at least 80 mole percent terephthalic and/or 2,6-naphthalenedicarboxylic acid residues;
(ii) diol residues comprised of at least 80 mole percent of the residue of a diol having the formula

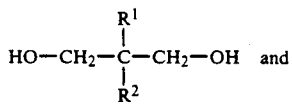

(iii) residues of one or more anthraquinone compounds having the formula

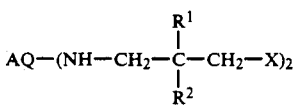

wherein

AQ is a 1,5- or 1,8-anthraquinonylene radical;
R$^1$ and R$^2$ each is methyl;
X is hydroxy, carboxy, or an ester group having the formula

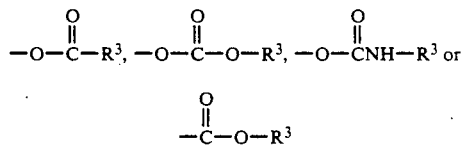

wherein R$^3$ is alkyl or phenyl, provided that component (iii) constitutes at least 0.5 weight percent of concentrate.

8. An amorphous color concentrate according to claim 7 wherein component (iii) constitutes about 10 to 40 weight percent of the concentrate.

9. An amorphous color concentrate according to claim 5 comprising a polyester having an inherent viscosity of 0.20 to 0.80 and a melting temperature of at least 110° C. comprised of:
(i) diacid residues consisting essentially of terephthalic and/or 2,6-naphthalenedicarboxylic acid residues;
(ii) diol residues consisting essentially of 2,2-dimethyl-1,3-propanediol residues; and
(iii) residues of an anthraquinone compound having the formula

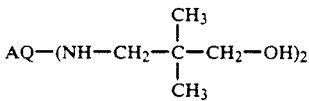

wherein AQ is a 1,5- or 1,8-anthraquinonylene radical; provided that component (iii) constitutes at least 0.5 weight percent of concentrate.

10. An amorphous color concentrate according to claim 7 wherein component (iii) constitutes about 10 to 40 weight percent of the concentrate.

11. A partially-crystalline polyester color concentrate comprised of:
(i) diacid residues consisting of at least 80 mole percent terephthalic acid residues, 2,6-naphthalenedicarboxylic acid residues, 1,3-cyclohexanedicarboxylic acid residues, 1,4-cyclohexanedicarboxylic acid residues or a mixture thereof;
(ii) diol residues consisting of at least 50 mole percent of residues having the formula —O—(CH$_2$)$_m$—O— wherein m is 4 to 12; and (iii) residues of one or more anthraquinone compounds having the formula

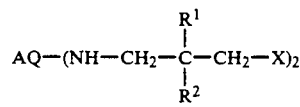

wherein

AQ is a 1,5- or 1,8-anthraquinonylene radical;
R$^1$ and R$^2$ are the same or different and are unsubstituted or substituted alkyl, cycloalkyl or aryl; and
X is a group reactive with at least one of the functional groups of the monomers from which the polyester is prepared, provided that component (iii) constitutes at least 0.5 weight percent of the concentrate.

12. A partially-crystalline polyester color concentrate according to claim 11 wherein
m is 4;
AQ is a 1,5- or 1,8-anthraquinonylene radical;
R$^1$ and R$^2$ are the same or different and are lower alkyl; and
X is hydroxy, carboxy, amino, alkyl amino or an ester group having the formula

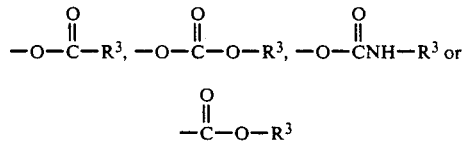

wherein R$^3$ is an unsubstituted or substituted alkyl, cycloalkyl or aryl radical, provided that component (iii) constitutes at least 0.5 weight percent of concentrate.

13. A partially-crystalline polyester color concentrate according to claim 11 comprised of:
(i) diacid residues consisting of at least 80 mole percent terephthalic acid residues;
(ii) diol residues consisting of at least 80 mole percent of residues of 1,4-butanediol; and
(iii) residues of one or more anthraquinone compounds having the formula

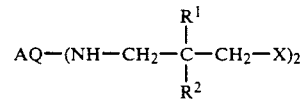

wherein

AQ is a 1,5- or 1,8-anthraquinonylene radical;
R$^1$ and R$^2$ each is methyl;
X is hydroxy, carboxy, or an ester group having the formula

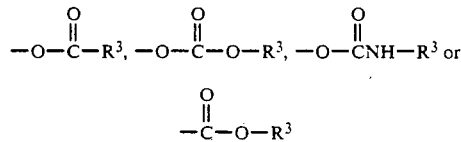

wherein R$^3$ is alkyl or phenyl, provided that component (iii) constitutes at least 0.5 weight percent of concentrate.

14. A partially-crystalline polyester color concentrate according to claim 13 wherein component (iii)

constitutes about 10 to 40 weight percent of the concentrate.

15. A partially-crystalline polyester color concentrate according to claim 11 having a melting temperature of at least 110° C. comprised of:
   (i) diacid residues consisting essentially of terephthalic acid residues;
   (ii) diol residues consisting essentially of 1,4-butanediol residues; and
   (iii) residues of an anthraquinone compound having the formula

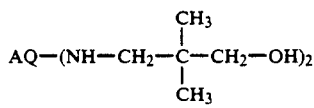

wherein AQ is a 1,5- or 1,8-anthraquinonylene radical; provided that component (iii) constitutes at least 0.5 weight percent of the concentrate.

16. A partially-crystalline polyester color concentrate according to claim 15 wherein component (iii) constitutes about 10 to 40 weight percent of the concentrate.

17. A colored semicrystalline powder having an average particle size of less than 30 microns comprising a normally-amorphous polyester which has been modified by dissolution-crystallization-precipitation to impart crystallinity thereto having copolymerized therein at least 0.5 weight percent, based on the weight of the concentrate, of the residue of one or more anthraquinone compounds having the formula

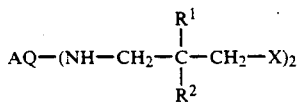

wherein
   AQ is a 1,5- or 1,8-anthraquinonylene radical;
   $R^1$ and $R^2$ are the same or different and are unsubstituted or substituted alkyl, cycloalkyl or aryl; and
   X is a group reactive with at least one of the functional groups of the monomers from which the polyester is prepared.

18. A colored semicrystalline powder according to claim 17 comprising a polyester having an inherent viscosity of at least 0.20 comprised of:
   (i) diacid residues comprised of at least 50 mole percent terephthalic and/or 2,6-naphthalenedicarboxylic acid residues;
   (iii) diol residues comprised of at least 50 mole percent of the residue of a diol having the formula

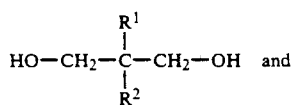

(iii) residues of one or more anthraquinone compounds having the formula

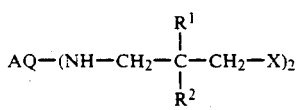

wherein
   AQ is a 1,5- or 1,8-anthraquinonylene radical;
   $R^1$ and $R^2$ are the same or different and are lower alkyl; and
   X is hydroxy, carboxy, amino, alkyl amino or an ester group having the formula

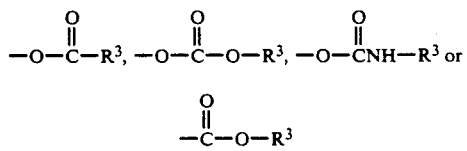

wherein $R^3$ is an uhsubstituted or substituted alkyl cycloalkyl or aryl radical, provided that component (iii) constitutes at least 0.5 weight percent of concentrate.

19. A colored semicrystalline powder according to claim 17 having an average particle size of less than 30 microns comprising a normally-amorphous polyester which has been modified by dissolution-crystallization-precipitation to impart crystallinity thereto comprised of:
   (i) diacid residues comprised of at least 80 mole percent terephthalic and/or 2,6-naphthalenedicarboxylic acid residues;
   (ii) diol residues comprised of at least 80 mole percent of the residue of a diol having the formula

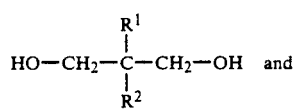

(iii) residues of one or more anthraquinone compounds having the formula

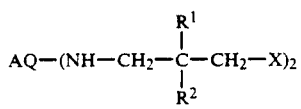

wherein
   AQ is a 1,5- or 1,8-anthraquinonylene radical;
   $R^1$ and $R^2$ each is methyl;
   X is hydroxy, carboxy, or an ester group having the formula

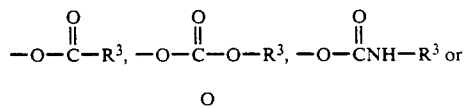

wherein $R^3$ alkyl or phenyl, provided that component (iii) constitutes at least 0.5 weight percent of concentrate.

20. A colored semicrystalline powder according to claim 17 wherein component (iii) constitutes about 10 to 40 weight percent of the concentrate.

21. A colored semicrystalline powder according to claim 17 having an average particle size of less than 30 microns comprising a normally-amorphous polyester which has been modified by dissolution-crystallization-precipitation to impart crystallinity thereto comprised of:

(i) diacid residues consisting essentially of terephthalic and/or 2,6-naphthalenedicarboxylic acid residues;
(ii) diol residues consisting essentially of 2,2-dimethyl-1,3-propanediol residues; and
(iii) residues of an anthraquinone compound having the formula

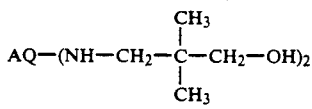

wherein AQ is a 1,5- or 1,8-anthraquinonylene radical; provided that component (iii) constitutes at least 0.5 weight percent of the concentrate.

22. A colored semicrystalline powder according to claim 21 wherein component (iii) constitutes about 10 to 40 weight percent of the concentrate.

23. A colored semicrystalline powder having an average particle size of less than 30 microns comprising a partially-crystalline polyester which had been modified by dissolution-crystallization-precipitation to impart increased crystallinity thereto comprised of:
(i) diacid residues consisting of at least 80 mole percent terephthalic acid residues, 2,6-naphthalenedicarboxylic acid residues, 1,3-cyclohexanedicarboxylic acid residues, 1,4-cyclohexanedicarboxylic acid residues or a mixture thereof;
(ii) diol residues consisting of at least 50 mole percent of residues having the formula $-O-(CH_2)_m-O-$ wherein m is 4 to 12; and
(iii) residues of one or more anthraquinone compounds having the formula

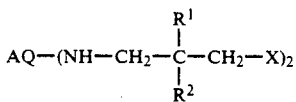

wherein
AQ is a 1,5- or 1,8-anthraquinonylene radical;
$R^1$ and $R^2$ are the same or different and are unsubstituted or substituted alkyl, cycloalkyl or aryl; and
X is a group reactive with at least one of the functional groups of the monomers from which the polyester is prepared, provided that component (iii) constitutes at least 0.5 weight percent of the concentrate.

24. A colored semicrystalline powder according to claim 23 wherein
m is 4;
AQ is a 1,5- or 1,8-anthraquinonylene radical;
$R^1$ and $R^2$ are the same or different and are lower alkyl; and
X is hydroxy, carboxy, amino, alkyl amino or an ester group having the formula

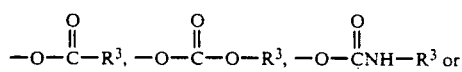

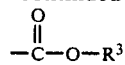

wherein $R^3$ is an unsubstituted or substituted alkyl, cycloalkyl or aryl radical, provided that component (iii) constitutes at least 0.5 weight percent of concentrate.

25. A colored semicrystalline powder according to claim 23 comprising a polyester having an inherent viscosity of at least 0.20 and a melting temperature of at least 110° C. comprised of:
(i) diacid residues consisting of at least 80 mole percent terephthalic acid residues;
(ii) diol residues consisting of at least 80 mole percent of residues of 1,4-butanediol; and
(iii) residues of one or more anthraquinone compounds having the formula

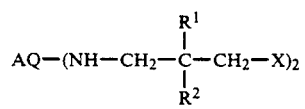

wherein
AQ is a 1,5-or 1,8-anthraquinonylene radical;
$R^1$ and $R^2$ each is methyl;
X is hydroxy, carboxy, or an ester group having the formula

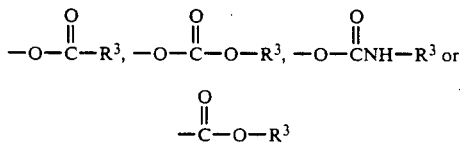

wherein $R^3$ is alkyl or phenyl, provided that component (iii) constitutes at least 0.5 weight percent of concentrate.

26. A colored semicrystalline powder according to claim 25 wherein component (iii) constitutes about 10 to 40 weight percent of the concentrate.

27. A colored semicrystalline powder according to claim 25 comprised of:
(i) diacid residues consisting essentially of terephthalic acid residues;
(ii) diol residues consisting essentially of 1,4-butanediol residues; and
(iii) residues of an anthraquinone compound having the formula

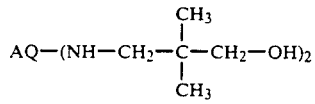

wherein AQ is a 1,5- or 1,8-anthraquinonylene radical; provided that component (iii) constitutes at least 0.5 weight percent of the concentrate.

28. A colored semicrystalline powder according to claim 27 wherein component (iii) constitutes about 10 to 40 weight percent of the concentrate.

* * * * *